United States Patent [19]
Halpern et al.

[11] Patent Number: 5,687,717
[45] Date of Patent: Nov. 18, 1997

[54] PATIENT MONITORING SYSTEM WITH CHASSIS MOUNTED OR REMOTELY OPERABLE MODULES AND PORTABLE COMPUTER

[75] Inventors: Arieh S. Halpern, Tarzana, Calif.; Anthony J. Aldrich, Philadelphia, Pa.

[73] Assignee: Tremont Medical, Inc., Aston, Pa.

[21] Appl. No.: 692,110

[22] Filed: Aug. 6, 1996

[51] Int. Cl.$^6$ ............................................. A61B 5/00
[52] U.S. Cl. ........................................ 128/630; 128/903
[58] Field of Search .................................. 128/630, 620, 128/671, 709, 710, 903, 904; 607/60; 364/413.02, 413.03

[56] References Cited

U.S. PATENT DOCUMENTS

| | | |
|---|---|---|
| 3,762,398 | 10/1973 | Schefke et al. |
| 3,857,383 | 12/1974 | Sommerfeld et al. |
| 3,860,000 | 1/1975 | Wooten et al. |
| 3,870,035 | 3/1975 | Sarnoff |
| 3,894,533 | 7/1975 | Cannon |
| 4,291,692 | 9/1981 | Bowman et al. |
| 4,300,550 | 11/1981 | Gandi et al. |
| 4,356,475 | 10/1982 | Neumann et al. ........................ 128/709 |
| 4,356,486 | 10/1982 | Mount |
| 4,366,818 | 1/1983 | Izumi |
| 4,403,984 | 9/1983 | Ash et al. |
| 4,414,982 | 11/1983 | Durkan |
| 4,449,538 | 5/1984 | Corbitt et al. |
| 4,494,950 | 1/1985 | Fischell |
| 4,534,756 | 8/1985 | Nelson |
| 4,584,989 | 4/1986 | Stith |
| 4,710,165 | 12/1987 | McNeil et al. |
| 4,715,385 | 12/1987 | Cudahy et al. |
| 4,803,625 | 2/1989 | Fu et al. |
| 4,813,427 | 3/1989 | Schlaefke et al. |
| 4,832,033 | 5/1989 | Maher et al. |
| 4,889,131 | 12/1989 | Salem et al. |
| 4,916,441 | 4/1990 | Gombrich |
| 4,957,121 | 9/1990 | Icenogle et al. |
| 5,036,852 | 8/1991 | Leishman |
| 5,088,981 | 2/1992 | Howson et al. |
| 5,101,820 | 4/1992 | Christopher |
| 5,142,484 | 8/1992 | Kaufman et al. |
| 5,343,869 | 9/1994 | Pross et al. |
| 5,375,604 | 12/1994 | Kelly et al. |
| 5,417,222 | 5/1995 | Dempsey et al. |
| 5,579,775 | 12/1996 | Dempsey et al. ........................ 128/903 |

FOREIGN PATENT DOCUMENTS

2215331   10/1973   Germany ................................ 128/630

OTHER PUBLICATIONS

SpaceLabs Medical, Inc. Corporate Profile, 12 pages plus front and back covers, published 1993.
SpaceLabs Medical, Inc. Form 10–K, 46 pages, published 1993.
Brochure–SpaceLabs Medical Inc. describing Medical Clinical Information Management Systems, 12 unnumbered pages, 1993.
Brochure for Datascope® point of view™ Critical Care Monitoring System–Mounting schemes, Datascope Corp. Paramus, NJ, 2 pages, brochure No. 0061–00–0631, publication date unknown, published prior to Aug. 6, 1995.
Brochure for Datascope® point of view™ Critical Care Monitoring System–OR/PACU, Datascope Corp. Paramus, NJ, 4 pages, brochure No. 0061–00–00632, publication daate unknown, published prior to Aug. 6, 1995.
Brochure for Datascope® point of view™ Critical Care Monitoring System–Transport, Datascope Corp. Paramus, NJ, 4 pages, brochure No. 0061–00–0633, publication date unknown, published prior to Aug. 6, 1995.
Brochure for Datascope®Passport™ El, Datascope Corp., Paramus, NJ, 2 pages, brochure No. 0061–00–0557–A, publication date unknown, published prior to Aug. 6, 1995.
Brochure for Datascope® Passport™ DFIB, Datascope Corp., Paramus, NJ, 2 pages, brochure No. 0061–00–0621, publication date unknown, published prior to Aug. 6, 1995.
Brochure for Datascope® Passport™ ER, Datascope Corp., Paramus, NJ, 2 pages, brochure No. 0061–00–0555–A, publication date unknown, published prior to Aug. 6, 1995.
Brochure for Datascope® Passport™ LCD, Datascope Corp., Paramus, NJ, 2 pages, brochure No. 0061–00–0597, publication date unknown, published prior to Aug. 6, 1995.

*Primary Examiner*—Jennifer Bahr
*Assistant Examiner*—Eric F. Winakur

*Attorney, Agent, or Firm*—Panitch, Schwarze, Jacobs & Nadel, P.C.

[57] ABSTRACT

A patient monitoring system includes one or more chassis, a plurality of patient care modules associated with the chassis, and a portable computer for communicating with, and controlling the modules. Each patient is assigned to a chassis, and each module is assigned to a patient and to a chassis. Each module is fully operational in either an independent or a dependent mode. In both modes, the chassis continuously polls the module for patient data collected by the module. In the dependent mode, the module is physically received by, and powered from, the chassis, and sends patient data to a computer in the chassis for storage therein. In the independent mode, the module is remote from, and independent of, the chassis. In the independent mode, the module stores patient data in its own memory when data cannot be communicated to the chassis. When requested by the portable computer, the chassis communicate the patient data to the portable computer. The portable computer may be connected to the chassis or may also be used remote from the chassis. The modules switch seamlessly between the independent and dependent modes with no loss of power or data. The system is arranged in a networked manner, with each chassis and each portable computer being a node on the network. A plurality of patients may be connected to the same chassis and the portable computer may simultaneously monitor a plurality of patients. The portable computer is adapted to set or modify module control parameters when the modules are in either the independent or the dependent mode.

26 Claims, 12 Drawing Sheets

PATIENT MONITORING SYSTEM WITH CHASSIS MOUNTED OR REMOTELY OPERABLE MODULES AND PORTABLE COMPUTER

CROSS REFERENCE TO RELATED APPLICATION

This application is related to U.S. Ser. No. 08/224,444, filed Apr. 7, 1994, entitled "PERSONAL HEALTH CARE SYSTEM", now U.S. Pat. No. 5,590,648, which is incorporated by reference in its entirety.

FIELD OF THE INVENTION

The present invention relates generally to patient monitoring systems for collecting, storing and displaying medical data and for controlling medical devices which perform such functions.

BACKGROUND OF THE INVENTION

Patient monitoring systems which reside at a patient's bedside and use dedicated bedside chassis for receiving a plurality of patient care modules are known in the art. One example of such a system is described in U.S. patent application Ser. No. 08/224,444, filed Apr. 7, 1994, entitled "PERSONAL HEALTH CARE SYSTEM". One disadvantage of such systems is that when it is desired to move or transport a patient, the dedicated chassis cannot be moved with the patient. Furthermore, the modules cannot be moved because they are incapable of being independently operated once removed from the chassis. Accordingly, a patient must temporarily forego certain care until the patient reaches another dedicated chassis having the appropriate modules. Alternatively, specialized portable modules may be used, if available, but the activity of such a portable module would not be monitored by the chassis. Another disadvantage of the dedicated chassis arrangement is that remote monitoring of modules is typically performed at a central station which is hardwired to each chassis. Thus, remotely located medical caregivers cannot effectively monitor and control modules in real time. Yet another disadvantage of dedicated chassis/module arrangements is that the modules cannot be easily and remotely reprogrammed. Patient monitoring systems which relate to some of the problems discussed above include U.S. Pat. No. 5,417,222 (Dempsey et al.); U.S. Pat. No. 4,916,441 (Gombrich); U.S. Pat. No. 5,343,869 (Pross et al.); U.S. Pat. No. 5,375,604 (Kelly et al.); U.S. Pat. No. 4,715,385 (Cudahy et al.); and U.S. Pat. No. 4,356,486 (Mount). Systems which use modules connected to a central system for patient monitoring are also disclosed in U.S. Pat. No. 4,803,625 (Fu et al.); U.S. Pat. No. 4,494,950 (Fischell); and U.S. Pat. No. 3,762,398 (Schefke et al.).

Despite the large number of patient monitoring systems known in the art, there is still a need for a system which allows modules to be used either within a chassis or in a completely independent manner, which allows modules to switch between a chassis mode and an independent mode in a seamless manner, and which allows modules to be continuously monitored and controlled in either mode at the chassis or at remote location in a wireless manner. The present invention fills these needs.

SUMMARY OF THE INVENTION

The present invention is a patient monitoring system which comprises one or more patient care modules, a point of care chassis adapted to communicate with one or more of the modules, and a portable computer also adapted to communicate with the one or more modules. The patient care modules are fully operational in either an independent or a dependent mode. The point of care chassis has a chassis computer and a power supply. Each chassis is adapted to physically receive and communicate with one or more of the modules for operating the modules in the dependent mode. In the dependent mode, the one or more modules are connected to the chassis computer and power supply. Each chassis is also adapted to remotely communicate with the one or more modules when operated in the independent mode. The portable computer communicates with the one or more modules when the one or more modules are in either the independent or dependent mode.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF PREFERRED EMBODIMENT

Figure 1:
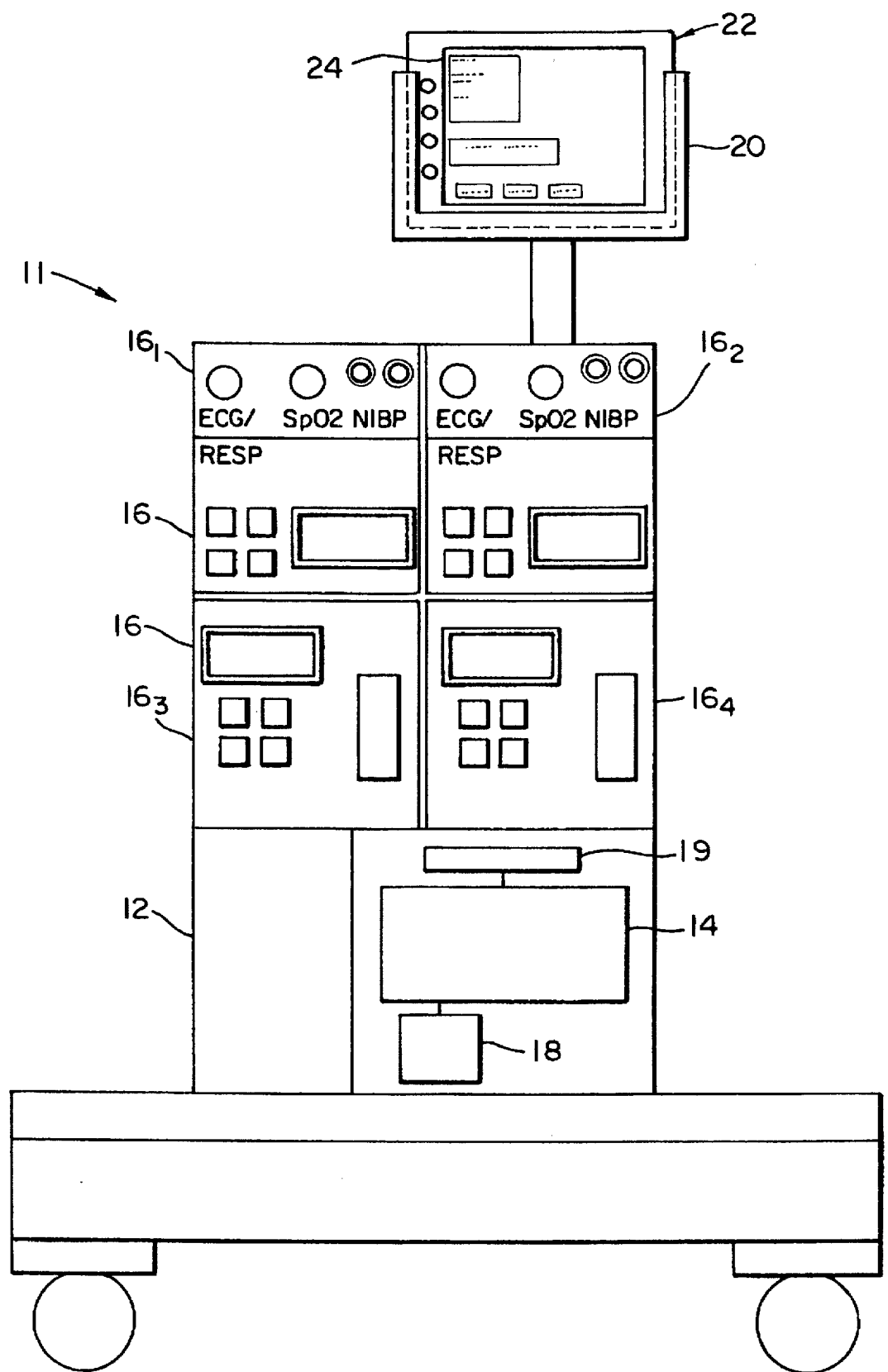
FIG. 1 is a front elevation view of a patient monitoring system configured in a first mode of operation, in accordance with a preferred embodiment of the present invention.

Certain terminology is used herein for convenience only and is not be taken as a limitation on the present invention. In the drawings, the same reference numerals are used for designating the same elements throughout the several figures.

Figure 2:
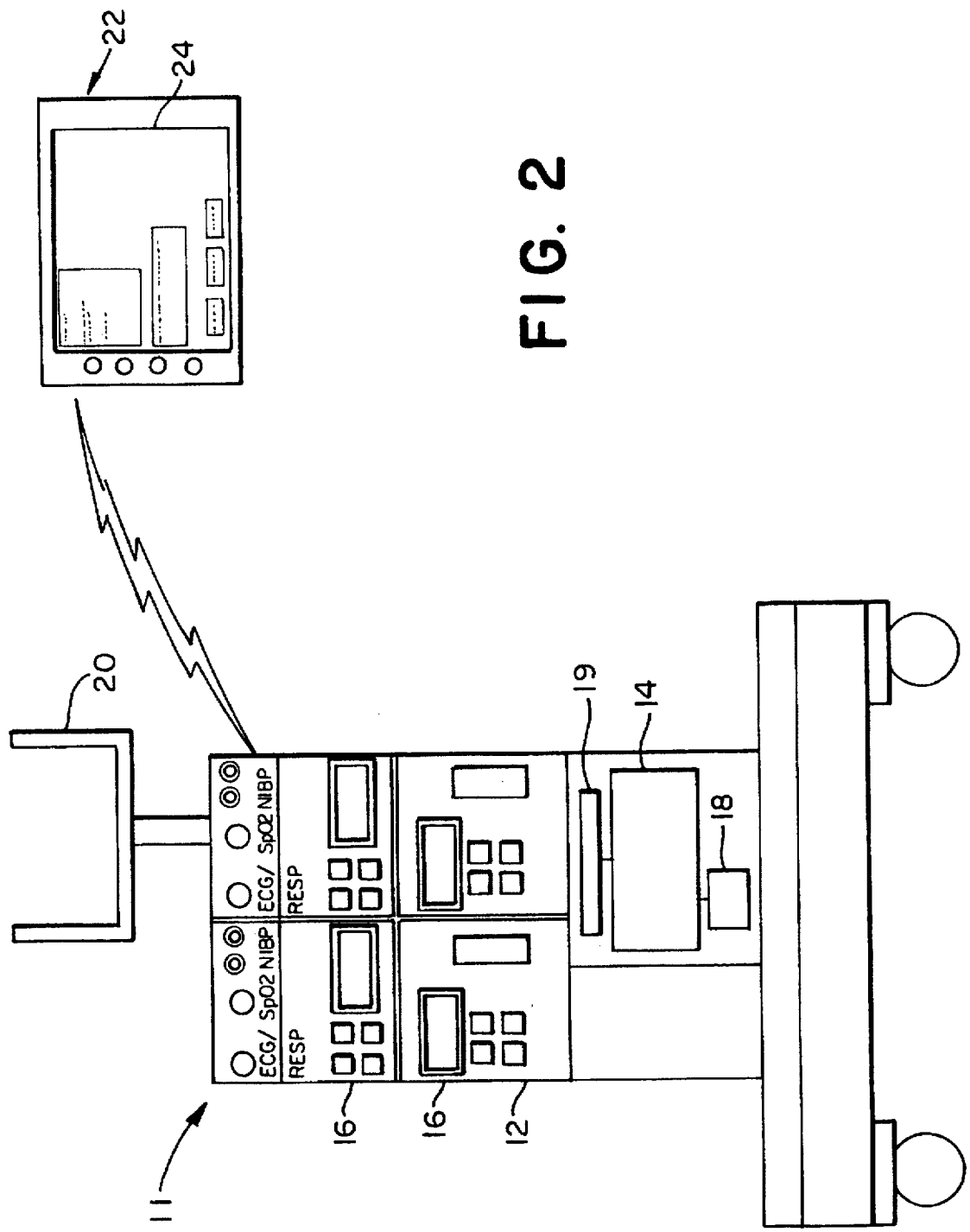
FIG. 2 is a front elevation view of the patient monitoring system configured in a second mode of operation.
Figure 3:
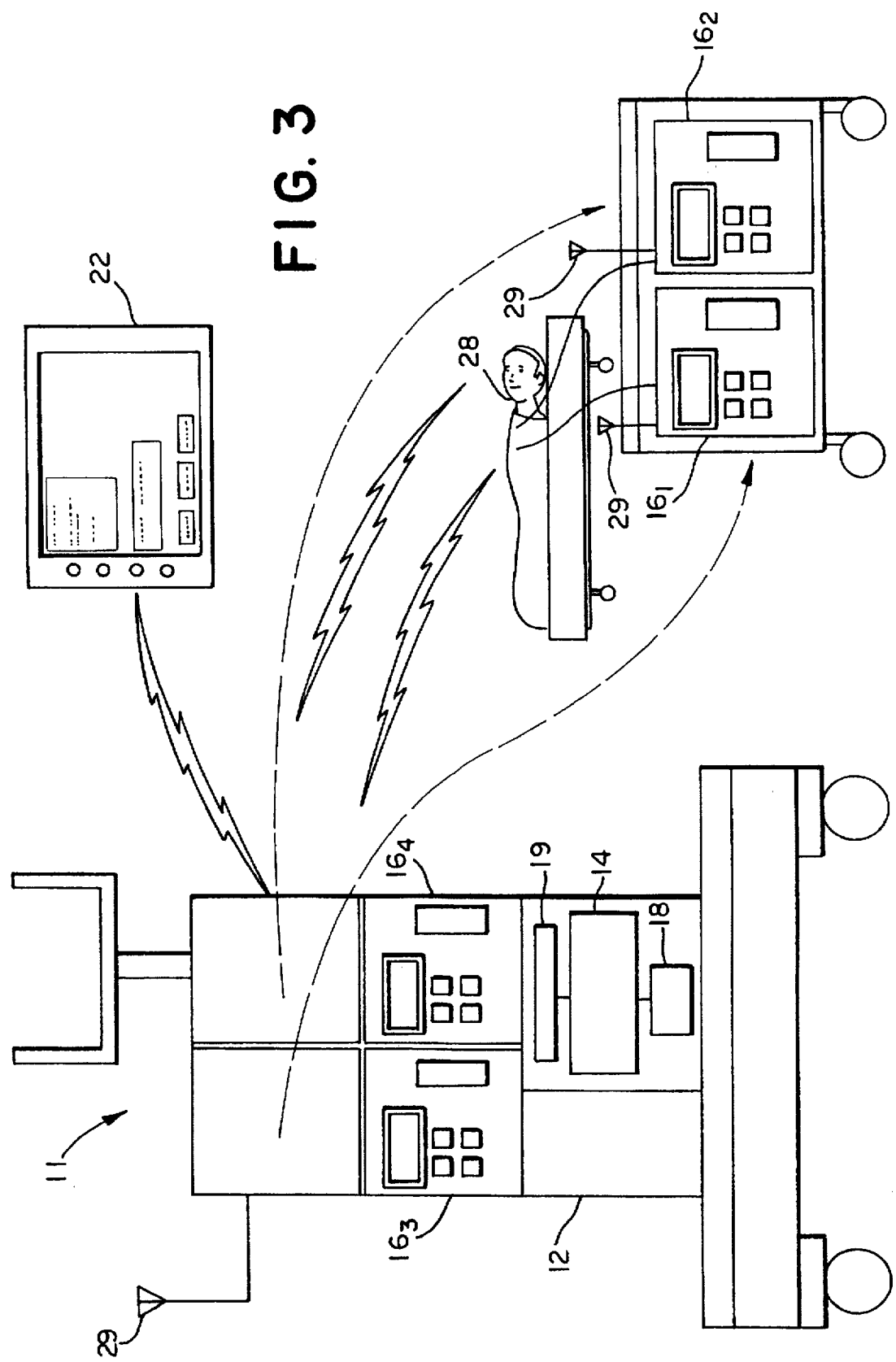
FIG. 3 is a front elevation and perspective view of the patient monitoring system configured in a third mode of operation.
Figure 4:
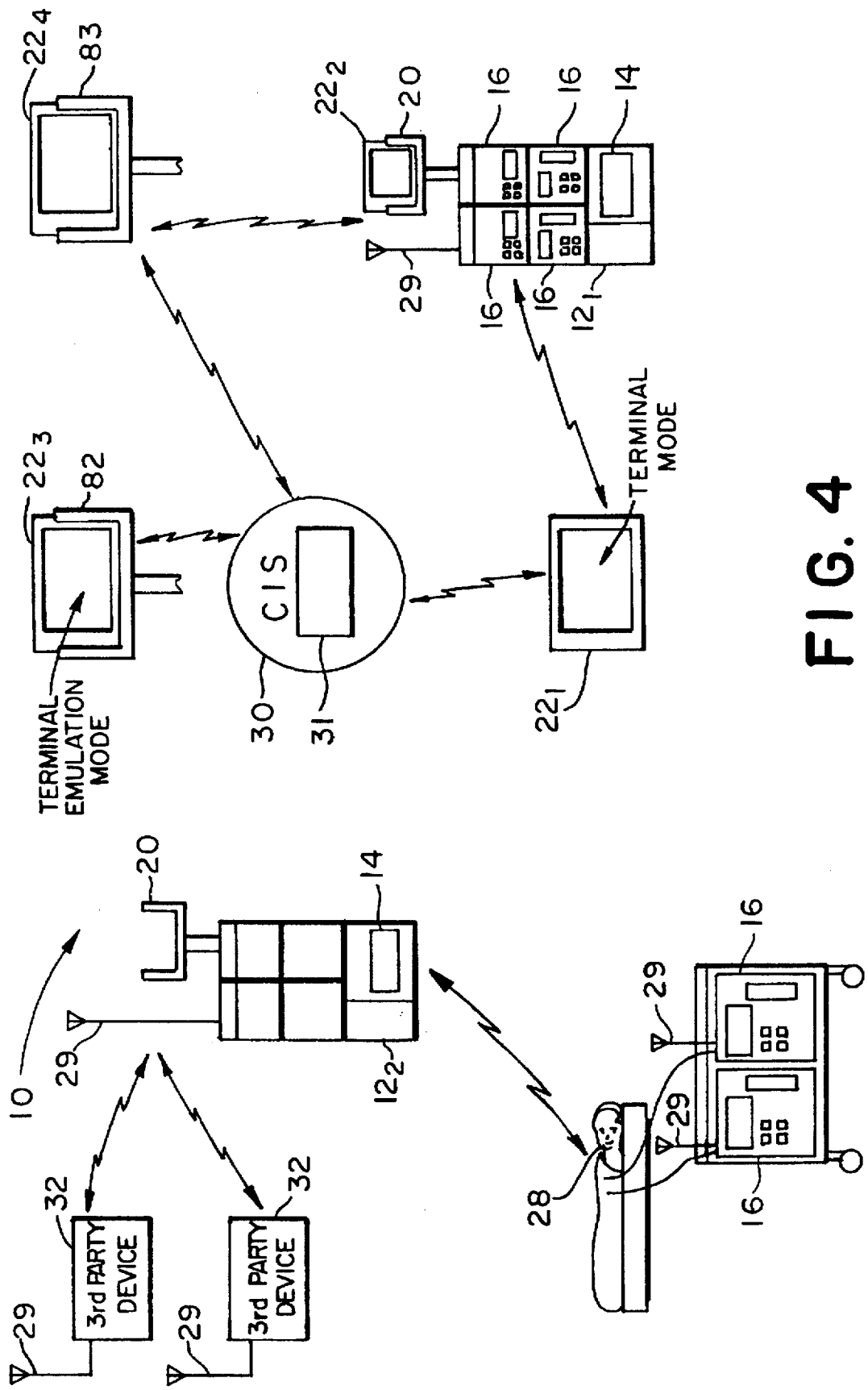
FIG. 4 is a schematic diagram of plural patient monitoring systems configured in a networked environment.

FIGS. 1–4 show pictorial representations of certain parts of a preferred embodiment of a patient monitoring system 10 in three different modes of operation. For simplicity, FIGS. 1–3 show one subsystem 11 of the overall system 10 and FIG. 4 shows the entire system 10 environment.

Referring to FIG. 1, the subsystem 11 includes a point of care chassis 12 having a chassis computer 14 housed therein. The chassis 12 receives one or more plug-in modules 16 for control and operation of the modules 16. Four such modules, 16₁–16₄, are shown in FIG. 1. The modules 16 provide patient care functions, and may include patient monitoring sensor modules, therapy-providing modules, or accessory modules. Accordingly, each module 16 includes appropriate input and output electrical leads, tubes, hoses, and the like which are directly connected to a patient. For simplicity, none of these parts are shown in FIG. 1. When the modules 16 are connected to the chassis 12, the modules 16 operate in a "dependent" or stationary mode. In the dependent mode, the modules 16 receive power from a power source (not shown) in the chassis 12, and receive control signals directly from the chassis computer 14. Patient data is displayed on a respective module 16 or on a chassis display (not shown). Patient data is also stored in a storage device 18 connected to the chassis computer 14. Thus, in the dependent mode, each module 16 communicates in a hardwired manner with the chassis computer 14. The chassis computer 14 includes a keyboard 19 and appropriate hardware and software to interface with the chassis computer 14 and to send control signals to the modules 16 to set the module operating parameters, such as alarm parameters and control functions. The keyboard 19 is preferably shock resistant and splash proof. Each chassis 12 is assigned to a particular patient, although plural patients may be assigned to a single chassis 12, as described below.

Prior to activating a module 16, the module 16 is assigned to a particular chassis 12 for subsequent location/ identification purposes. Thus, each module 16 becomes a child of its assigned parent chassis 12. Furthermore, each module 16 contains a unique assigned identification (ID) code which is used as its address. When a module 16 is brought into service, it is also assigned to a specific patient. A computer in each module 16 thus tracks the chassis 12 and patient associated with each module.

Figure 7:
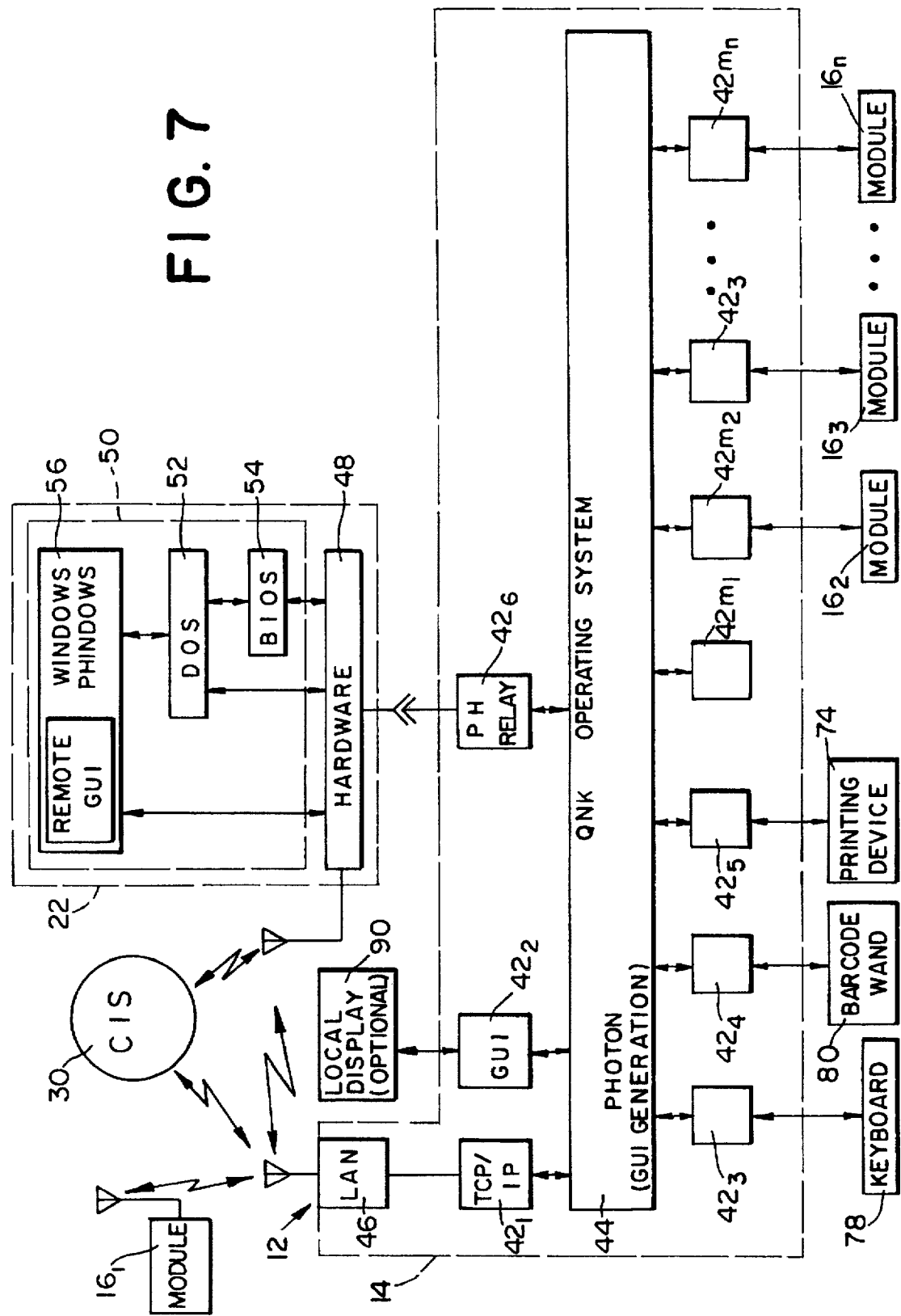
FIG. 7 is a schematic block diagram of the hardware and software components of the patient monitoring system.

Referring to FIGS. 4 and 7, a plurality of chassis 12 may be connected in a network arrangement, each chassis 12 being a node on a common local area network (LAN). The assignments, ID codes and patient names are tracked by a clinical information system (CIS) 30, which is another node on the network. A sample assignment scheme may contain the following information regarding chassis and modules:
Chassis ID no. 101—Patient no. 960812345 (Jones)
Chassis ID no. 102—Patient no. 980710066 (Williams)
Module ID no. 1001 (pulse oximeter) assigned to:
 Chassis 101
 Patient no. 960812345 (Jones)
Module ID no. 1002 (pulse oximeter) assigned to:
 Chassis 102
 Patient no. 960710066 (Williams)
Module ID no. 2001 (blood pressure monitor) assigned to:
 Chassis 101
 Patient no. 960812345 (Jones)
Module ID no. 2002 (blood pressure monitor) assigned to:
 Chassis 102
 Patient no. 960710066 (Williams)
Module ID no. 3001 (heart rate monitor) assigned to:
 Chassis 101
 Patient no. 960812345 (Jones)
Module ID no. 3002 (heart rate monitor) assigned to:
 Chassis 102
 Patient no. 960710066 (Williams)

In the example above, the chassis 101 is assigned to patient Jones. Three different types of modules 16 are assigned to Jones and to the chassis 101. Modules 1001, 2001 and 3001 communicate only with chassis 101, whether in the independent or dependent mode. Likewise, the chassis 102 is assigned to patient Williams. Three different types of modules 16 are assigned to Williams and to the chassis 102. Modules 1002, 2002 and 3002 communicate only with chassis 102, whether in the independent or dependent mode.

In an alternative embodiment of the invention, a single chassis may be assigned to more than one patient. For example, two patients may be assigned to a single chassis. The typical practice today is to assign one entire bedside monitoring system to each patient even if the patient uses only a small amount of the capacity of the system. Significant cost savings are possible by sharing a chassis 12 with more than one patient, such as patients who are physically adjacent to each other on the hospital floor. Of course, plural patients are assigned to the same chassis 12 only if there is sufficient capacity to accommodate all of the module needs of the plural patients. In one embodiment of the invention, the left side of the chassis 12 (i.e., the module receiving bays or slots on the left side of the chassis 12 and any modules 16 plugged therein) is assigned to a first patient, and the right side of the chassis 12 (i.e., the module receiving bays or slots on the right side of the chassis 12 and any modules 16 plugged therein) is assigned to a second patient. Using the example of chassis and module assignments above, if Jones and Williams require only two monitors each (pulse oximeter and heart rate monitor), an assignment scheme would look like the following:
Chassis ID no. 101L—Patient no. 960812345 (Jones)
Chassis ID no. 101R—Patient no. 980710066 (Williams)
Module ID no. 1001(pulse oximeter) assigned to:
 Chassis 101
 Patient no. 960812345 (Jones)
Module ID no. 1002 (pulse oximeter) assigned to:
 Chassis 101
 Patient no. 960710066 (Williams)
Module ID no. 2001 (blood pressure monitor) assigned to:
 Chassis 101
 Patient no. 960812345 (Jones)
Module ID no. 2002 (blood pressure monitor) assigned to:
 Chassis 101
 Patient no. 960710066 (Williams)

Figure 10:
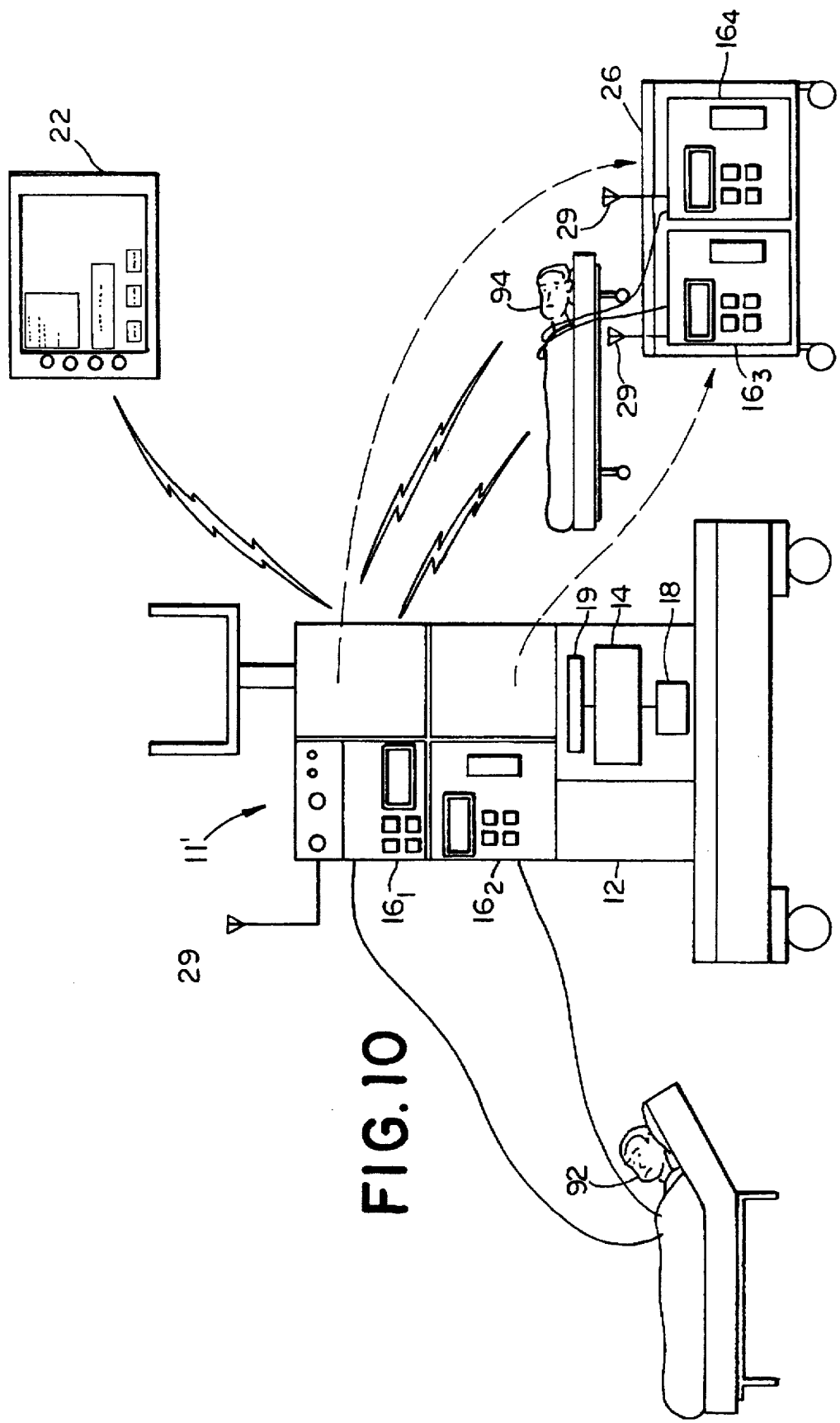
FIG. 10 is a front elevation and perspective view of the patient monitoring system configured in an alternative embodiment of the invention wherein plural patients share a single chassis.

In the chassis sharing configuration, software within the chassis 12 allocates separate memory locations for each patient and directs the patient data received from the modules 16 to the appropriate memory locations. FIG. 10 shows an example of a chassis sharing configuration and is described in further detail below.

To assign a module 16, a medical caregiver or clinician user inserts an unassigned module 16 into a bay of the chassis 12, thereby placing the module 16 in a module-standby state. Next, the clinician user inputs the module identification number and the patient identification number into the chassis computer 14. If the inputs are valid and accepted, the module 16 becomes assigned to the patient and to the respective chassis 12, and the module 16 is activated for receiving patient data. To unassign a module 16, the clinician user inserts the assigned module 16 into the chassis 12 (if the module 16 is not already in the chassis) and reenters the module identification number and the patient identification number into the chassis computer 14. If the inputs are valid and accepted, the module 16 becomes unassigned and returns to the module-standby state.

The assignments, ID codes and patient names are tracked by the CIS 30. Each chassis 12 also stores data regarding the modules 16 and patients assigned thereto.

Referring again to FIG. 1, the subsystem 11 also includes a docking station 20 which is preferably physically attached to the chassis 12 and preferably hardwired to the chassis computer 14 for facilitating communication therebetween. In one embodiment of the present invention, the docking station 20 has no significant hardware or software and functions merely as an I/O connection port for communication with the chassis computer 14, or for communication with the modules 16 through the chassis computer 14. In another embodiment of the invention, the docking station 20 has optional built-in intelligence in the form of hardware and/or software for providing additional functions, such as a mouse, external display, and an external storage medium (e.g., floppy or hard disk, RAM cards, CD player). For simplicity, the optional components are not shown.

Still referring to FIG. 1, the subsystem 11 further includes a portable computer 22. The docking station 20 is configured to physically receive and hold in place the portable computer 22, and to electrically connect the portable computer 22 to the docking station connection port. In the disclosed embodiment of the invention, the docking station 20 has a pod-like configuration for physically receiving the portable computer 22 therein. However, the docking station 20 can have other configurations which provide the necessary holding and connection functions. When the portable computer 22 is "hard docked" (i.e., attached) to the docking station 20, it communicates directly with the chassis computer 14, and with the modules 16 through the chassis computer 14. The portable computer 22 includes a prominent CRT-type display 24 and a dedicated processor (not shown). The display 24 may optionally be a touch screen to facilitate inputting of information by use of fingers or a light pen. The portable computer 22 optionally includes other forms of well-known user interfaces, including a keyboard, a mouse and voice recognition circuitry.

The portable computer 22 includes appropriate hardware and software to perform at least the following functions relevant to the subsystem 11 shown in FIG. 1:

(1) Monitor and/or store patient data collected by the modules 16. Monitoring may be performed in either real-time, or on a historical basis;

(2) Send control signals to the modules 16 to set or modify the module operating parameters. A graphical user interface (GUI) display mode is preferably used for this purpose;

(3) Receive alarm signals from the modules 16 when a module 16 detects an alarm condition. (An alarm condition occurs when patient data is outside of a predetermined range.)

Additional functions of the portable computer 16 are described below. Optionally, the chassis computer 14 may include a local display (not shown) having a GUI display mode for allowing a clinician user to send control signals to the modules 16 to modify the module operating parameters, thereby eliminating the need to have a portable computer 22 for the modification function. However, the local display should not be used if the hospital wants to maintain tight security regarding module operating parameters. Instead, modifications should be permitted only through the portable computer 22 which is issued to selected persons.

FIG. 2 shows a second mode of operation for the subsystem 11. In the second mode, the portable computer 22 is not hard-docked. Instead, the portable computer 22 operates remotely, and communicates in a bidirectional, wireless manner with the chassis computer 14. The functional capabilities of the portable computer 22 in the second mode are identical to those in the first mode. One advantage of the second mode is that a clinician user can interact with the modules 16 without being physically located at a patient's bedside. In the remote mode, the clinician user must input a patient name, chassis number, or module ID code into the portable computer 22 before a request for data is sent. Likewise, the clinician user must designate the module ID when a request is made to change a module control parameter.

FIG. 3 shows a third mode of operation for the subsystem 11 and illustrates an important feature of the invention, namely the ability of modules 16 to be fully operational in an "independent" or ambulatory mode (i.e., unconnected to the chassis 12). The portable computer 22 may continue to monitor and/or control the modules 16 while the portable computer 22 and the modules 16 are operating remotely. FIG. 3 shows an example wherein two of the modules, $16_1$ and $16_2$, are removed from the chassis 12 and placed on a transport cart 26 to be moved with patient 28 to a location remote from the chassis 12, such as a lab, surgery room, ambulance, or new bed. The third mode of operation thus allows a patient to be continuously monitored in a remote (wireless) manner when hardwired communications with modules 16 or a chassis 12 are impractical or impossible to maintain.

To facilitate the third mode of operation, the modules 16 are configured to provide the same functions as when they are hardwired to the chassis 12. Thus, each module 16 includes an independent power source, processor/controller device, display, storage device and input device. However, it is not necessary for the modules 16 to have the same capability or capacity as the capability or capacity of the module/chassis combination (FIG. 1 mode of operation), because the modules 16 are typically operated in the remote mode for only a short period of time. Thus, the capacity of the chassis power source (power output and operating time), chassis display, if used, (display size and features) chassis storage device (memory size) and chassis input device (types of devices and number of input ports) is typically greater than the capacity of the related module parts when operated independently. The remote (independent) modules 16 and the chassis 12 are each equipped with an antenna 29 and appropriate transceiver circuitry (not shown) for allowing wireless communication between the remote modules 16 and the chassis computer 14. The remotely located portable computer 22 may thus interact with the remote modules 16, through the chassis computer 14, in the same manner as when the modules 16 are hardwired to the chassis 12. In an alternative scheme (not shown), the remotely located portable computer 22 directly communicates with the remote modules 16.

FIG. 4 shows a system diagram of one environment for the components in the system 10, and illustrates the flexibility of the present invention. Each medical facility includes a plurality of chassis 12/docking station 20 assemblies. Each chassis 12 includes an antenna 29 and appropriate transceiver circuitry (not shown) for allowing its chassis computer 14 to remotely communicate with a clinical information system (CIS) 30. The CIS 30 contains a central computer in the form of a file server 31 which maintains all patient file records. At any one time, each of the modules 16 currently in service operates in either a dependent or independent mode. In FIG. 4, the modules 16 associated with chassis $12_1$ are in an independent mode servicing patient 28, and the modules 16 associated with chassis $12_2$ are in a dependent mode servicing a bedside patient (not shown). A plurality of portable computers 22 operate in the system 10. Each portable computer 22 is either in a docking station 20 or is being operated remotely. In FIG. 4, one portable computer $22_1$ is being operated remotely, and another portable computer $22_2$ is in a docking station 20 of the chassis $12_1$. Other remote portable computers 22 may be used in the system 10. Each portable computer 22 is identical and interchangeable with each other. That is, the portable computers are not preassigned to, or associated with, a particular chassis 12. The number of portable computers 22 in the system 10 thus need not be the same as the number of chassis 12. For example, there may be more portable computers 22 than chassis 12. Each remote portable computer 22 communicates with the desired chassis computers 14 to gain access to the independent and dependent modules 16. The portable computer 22 may communicate with any grouping of independent and dependent modules 16 from the same or different chassis or patients. Furthermore, more than one portable computer 22 may simultaneously retrieve data from a particular module 16. In this manner, a patient may be simultaneously monitored by more than one person. However, only one portable computer at a time may send control signals to a module 16 to set or modify the module operating parameters. Also, there may be additional docking stations which are not associated with a particular chassis 12. A mobile chart docking station 82 may allow direct access by a portable computer $22_3$ to the CIS 30 for retrieval of patient charts. A permanent docking station 83 may also allow direct access by the portable computer 22 to the CIS 30 for retrieval of patient charts. The permanent docking station 83 may also be used to communicate between a portable computer $22_4$ and a chassis 12. The permanent docking station 83 differs from the mobile chart docking station 82 in that the permanent docking station 83 provides an independent source of power to the portable computer $22_4$, as well as wireless communications means for the portable computer $22_4$. Thus, a permanent docking station 83 may be used with a portable computer $22_4$ that is not equipped with an independent source of power and/or wireless communications means.

FIG. 4 also illustrates additional features of the present invention when used in a system configuration. One additional feature of the present invention is that the portable computer 22 may emulate a workstation or terminal to interface with the file server 31 of the CIS 30. This feature is illustrated by showing a remote communication link between portable computer $22_3$ and the CIS 30.

Another additional feature is that one or more third party medical devices 32 which collect patient data may be integrated into the system 10. The devices 32 may be used alongside the modules 16 in an independent mode. The devices 32 are not fully compatible with the protocols of the modules 16 and do not have share the appropriate lower level hardware and software architecture. Accordingly, these devices cannot be "controlled" in the same manner as the modules 16. However, the devices 32 are configured to use the same communication protocol as the modules 16. Accordingly, patient data collected by the third party devices 32 may be remotely transmitted to a chassis 12 for ultimate retrieval and passive monitoring by a portable computer 22.

Figure 5:
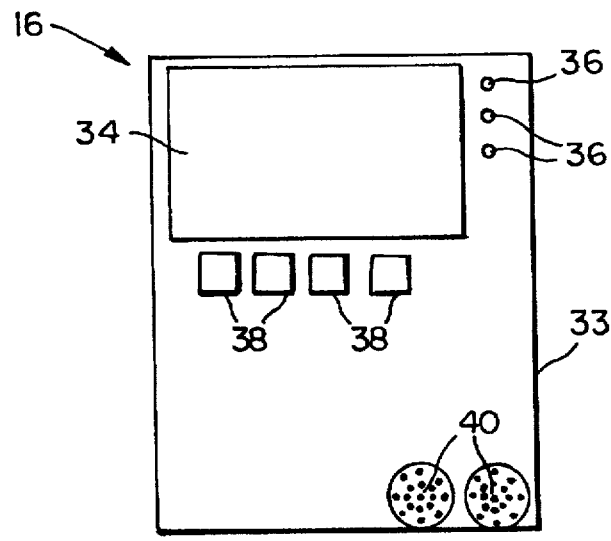
FIG. 5 is a front elevation view of a front panel of a module-for use in the patient monitoring system.
Figure 6:
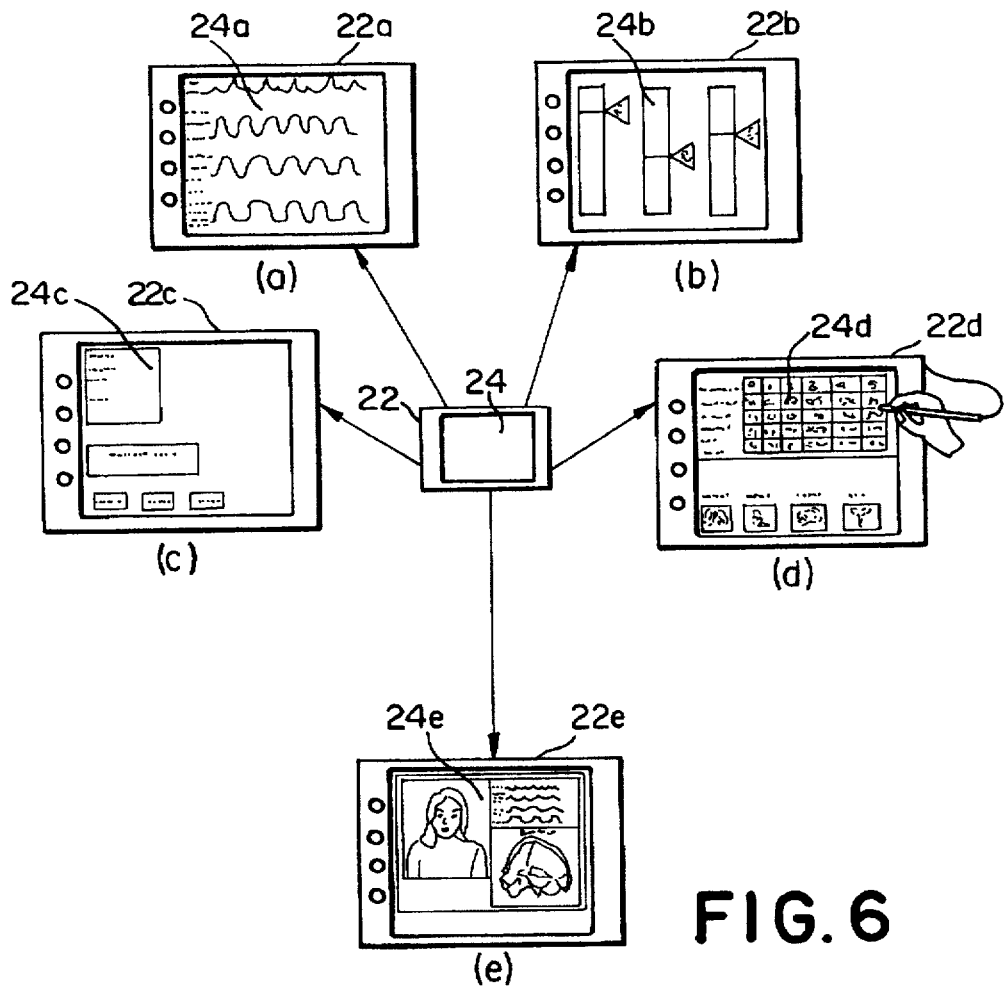
FIGS. 6A–6E shows screen displays associated with a portable computer for use in the patient monitoring system.
Figure 6A:
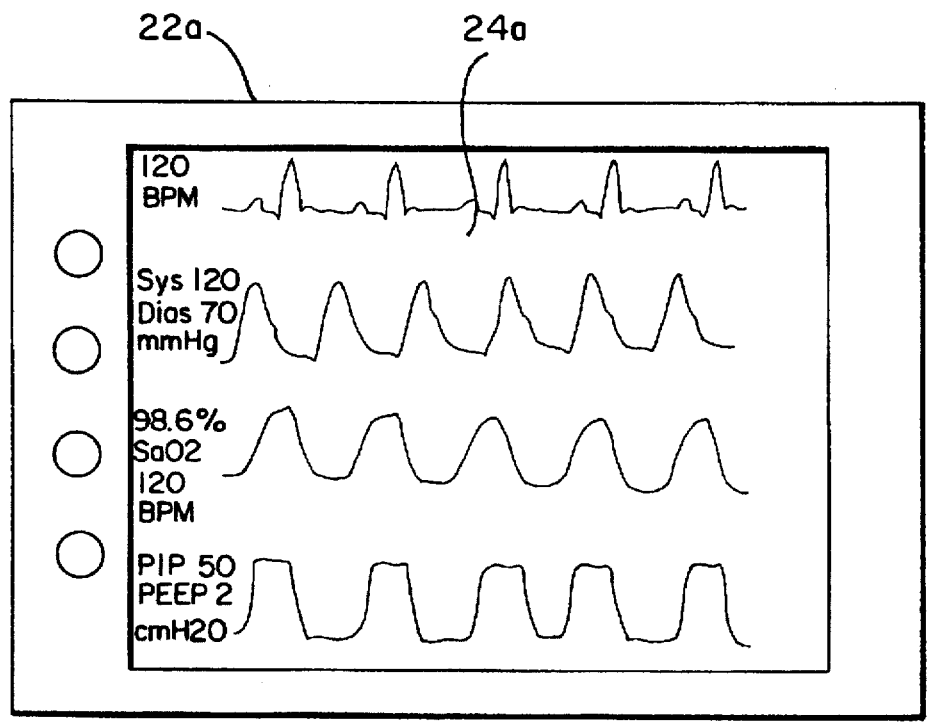
Figure 6B:
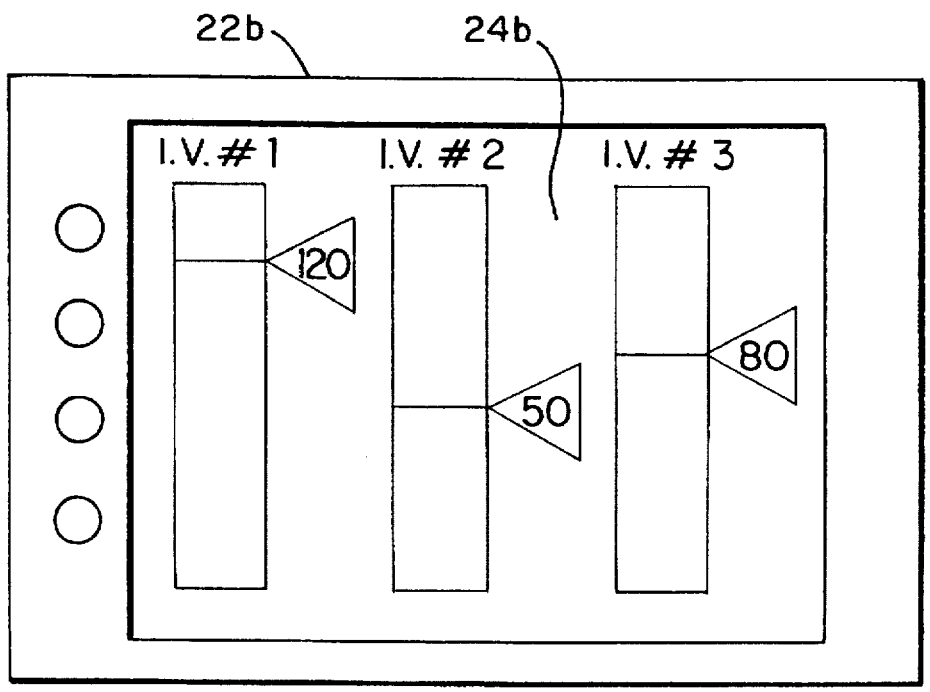
Figure 6C:
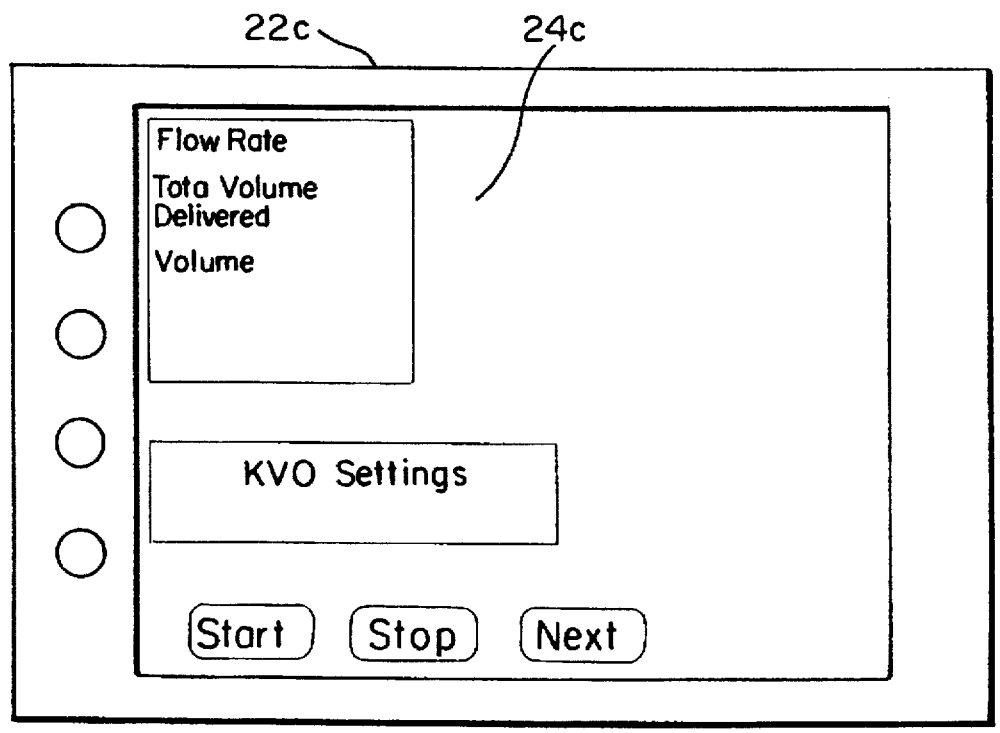
Figure 6D:
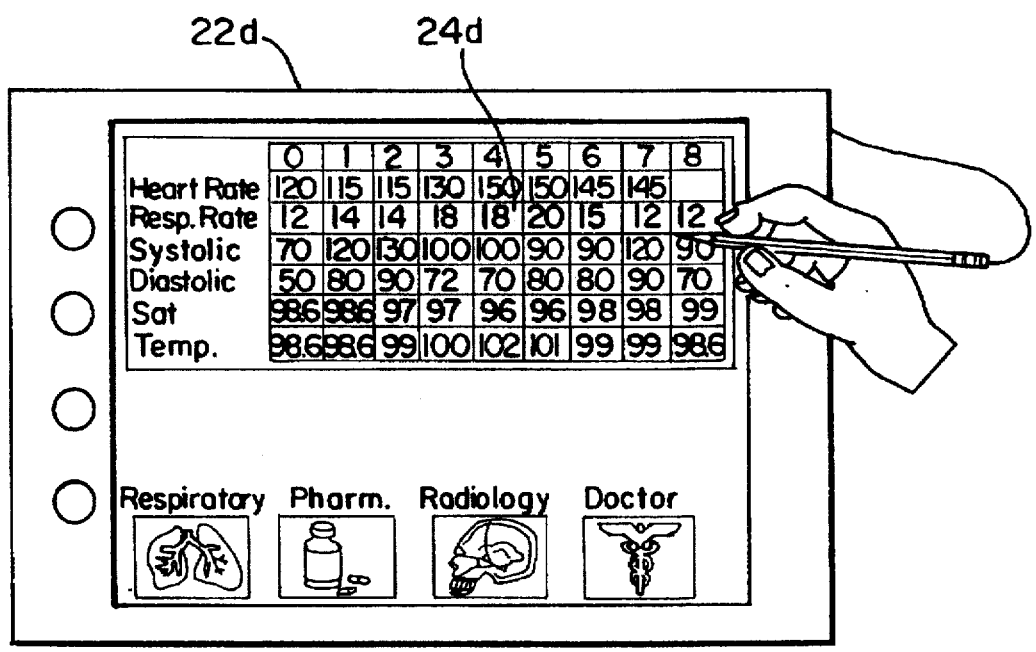
Figure 6E:
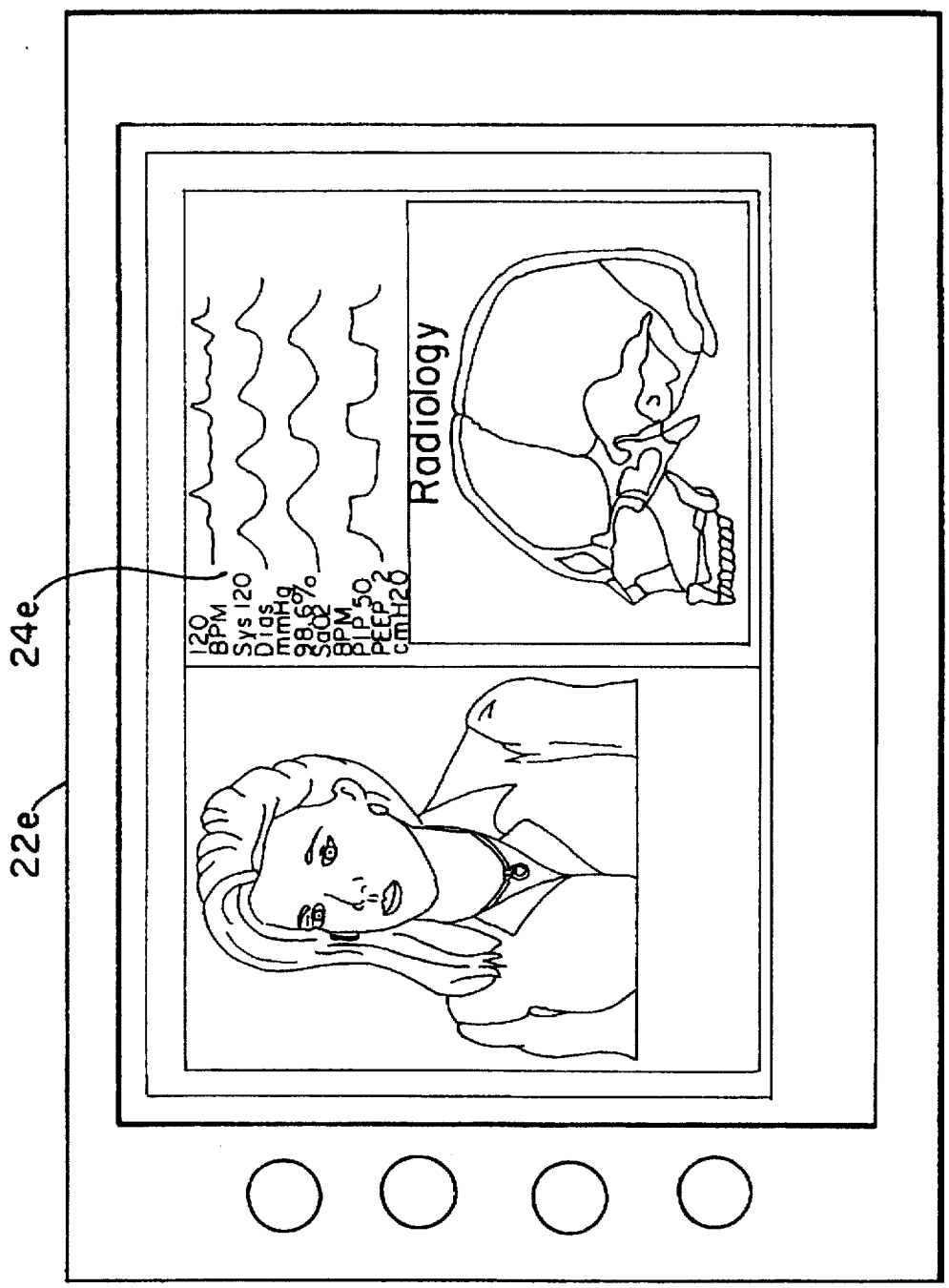
Figure 8A:
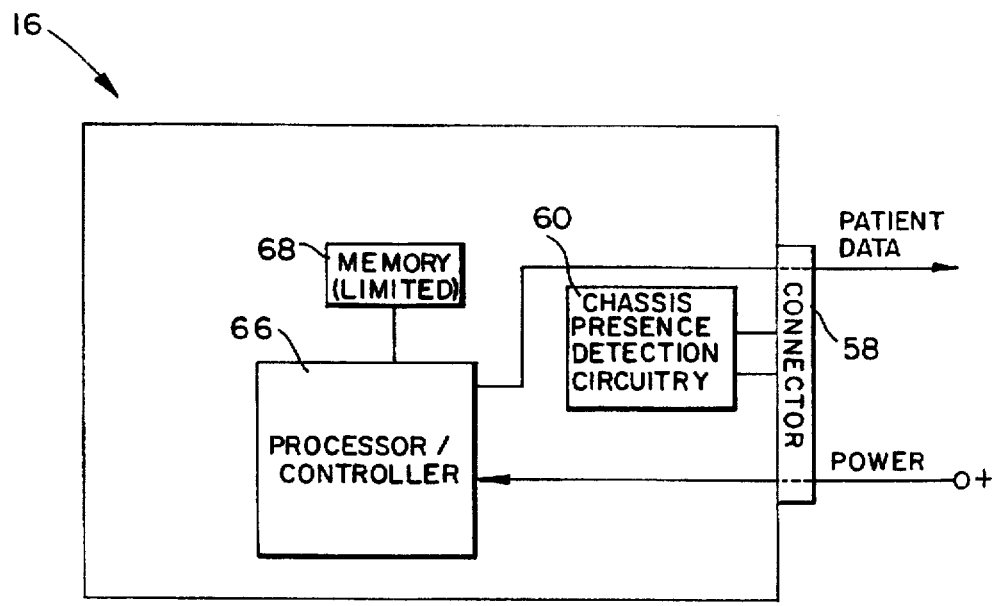
FIGS. 8A and 8B are schematic block diagrams of the module for use in the patient monitoring system.
Figure 8B:
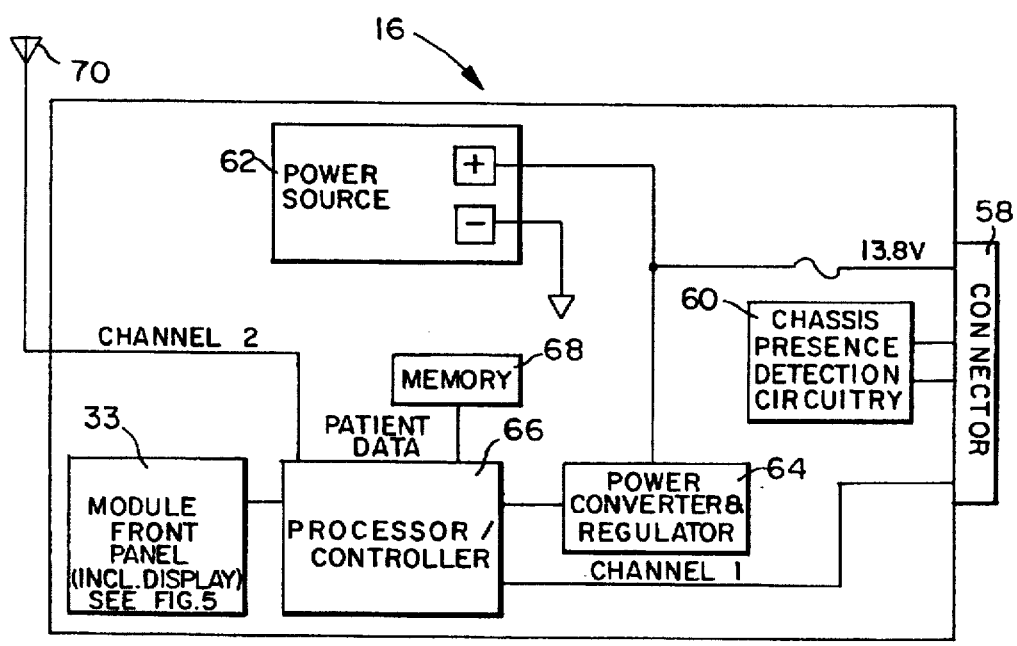

FIG. 5 shows a front panel 33 of a generic patient monitoring sensor-type module 16 suitable for use in the present invention. The module 16 includes a display 34, status indicators 36, control keys 38, and patient input connectors 40 for receiving ECG, NIBP (non-invasive blood pressure), or pulse oximetry ($SpO_2$) leads, or the like. Internal hardware components of the module 16 are shown in FIGS. 8A and 8B.

FIGS. 6 and 6A-6E show examples of screen displays available on the portable computer's display 24, depending upon the mode of the portable computer 22. In screen (a), shown in detail in FIG. 6A, a patient's vital signs are monitored in real-time, the vital signs being measured by a plurality of modules 16. In screen (b), shown in detail in FIG. 6B, IV infusion data is displayed in real-time, as obtained from infusion modules 16. In screen (c), shown in detail in FIG. 6C, a controller mode allows the portable computer 22 to be used as a controller to set or modify operating parameters of a module 16. The controller mode may optionally use a graphical user interface to simplify the process. In screen (d), shown in detail in FIG. 6D, a terminal emulation mode allows the portable computer 22 to view data from, and enter data into, the CIS 30. In screen (e), shown in detail in FIG. 6E, a split-screen display simultaneously shows different types of information. For example, one portion of the display 24 may show vital signs data, another portion may be used for video, and another portion may show medical images. In this manner, clinician users can remotely monitor and diagnose a patient's condition while simultaneously discussing the patient with another party using peer-to-peer video conferencing. In sum, the display 24 may present any type of data available within the system 10, including, but not limited to, (a) static data (i.e., alphanumeric characters such as heart rate, respiratory rate, blood pressure values), (b) dynamic data (i.e., real time morphological waveforms such as ECG, EKG, EEG waveforms), or (c) image data, such as ultrasound, CAT or x-ray images, or video images.

Figure 9:
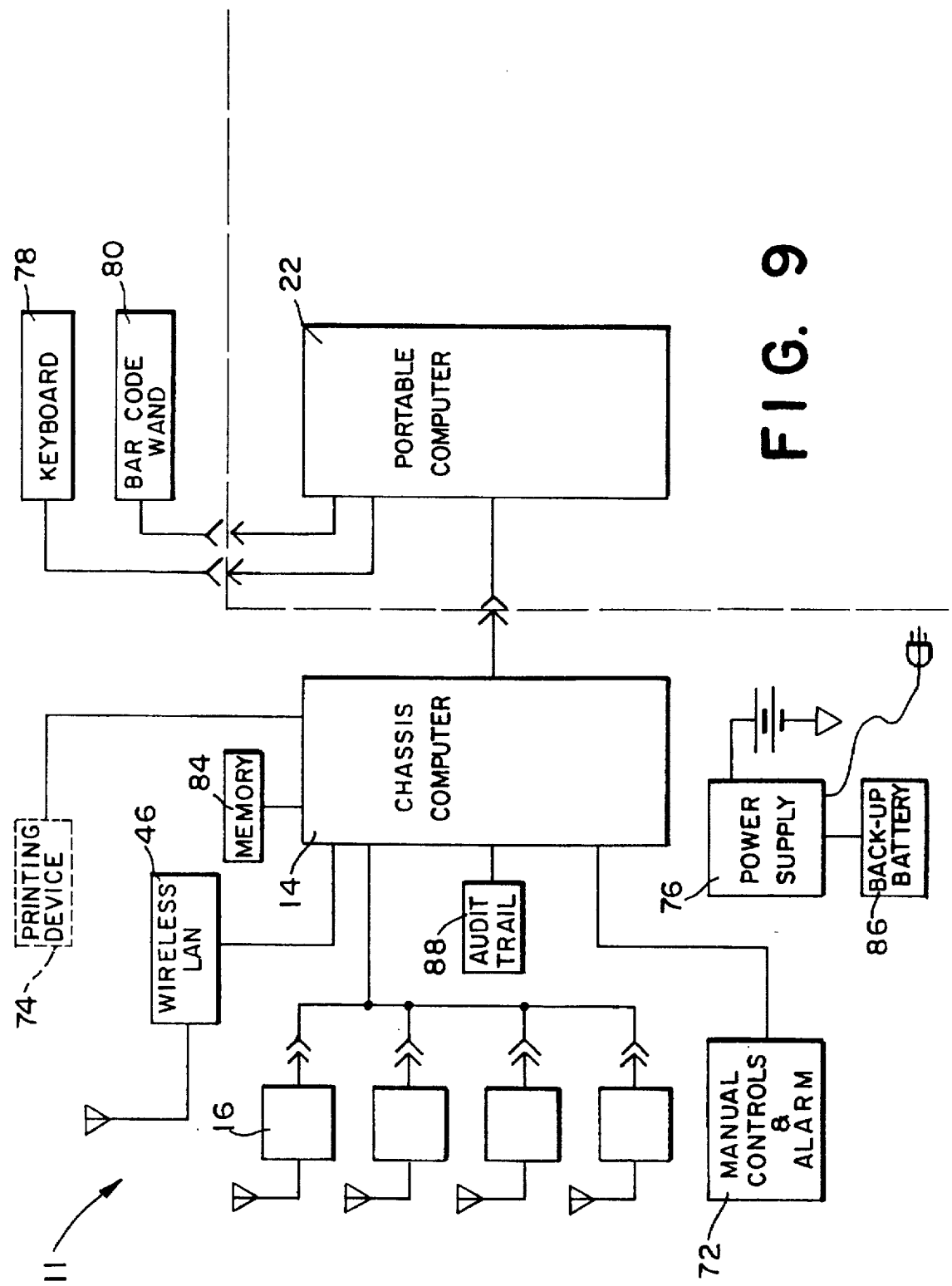
FIG. 9 is a schematic block diagram of the patient monitoring system.

Having described the overall environment of the present invention, specific details of the hardware and software for the system 10 and subsystem 11 are explained next with respect to FIGS. 7–9. FIGS. 7 and 9 are schematic block diagrams of the system 10. FIGS. 8A and 8B are schematic block diagrams of one module 16.

FIG. 7 shows a point of care chassis 12, a hard docked portable computer 22, an independent module $16_1$ in wireless serial communication with its parent chassis 12, a plurality of dependent modules $16_2$, $16_3$, . . . $16_n$, plugged into their parent chassis 12 for communication with chassis computer 14, and a CIS 30. Both the chassis 12 and the portable computer 22 are in wireless serial communication with the CIS 30. The communications system operates in an Internet-like environment. The plurality of chassis 12, each portable computer 22, and the CIS 30 are nodes in a network. All nodes conform to the industry standard UNIX 4.3 BSD socket syntax to establish communications with other nodes on the network. Communications between components are accomplished using standard TCP/IP protocols. Thus, each node distinguishes itself from the other nodes by its IP address, which is a unique 32 bit value. Communications preferably occur using RS-232 links.

The chassis computer 14 of the chassis 12 includes a plurality of software processes and programs 42 executed by a real-time operating system 44 which has a kernel in protected memory. One preferred operating system 44 is QNK, available from QNK, Inc., Ontario, Canada. One software process $42_1$ executes the TCP/IP protocols and is connected to LAN communication hardware 46. Another software process $42_2$ executes a graphical user interface (GUI) for use with the portable computer 22, as described below. Another set of software processes $42_{m1}$, $42_{m2}$ and so on, contain complete control programs for respective modules 16. Other software processes $42_3$, $42_4$ and $42_5$ control external devices, including a keyboard 78, bar code wand 80 and printing device 74, respectively. These external devices are described further below with respect to FIG. 9.

The portable computer 22 includes appropriate hardware 48 and software 50 for performing all of its functions. The hardware 48 includes memory, hardwired and remote communications circuitry and input/output ports for hard docking with the chassis 12. The software operating systems include DOS 52/BIOS 54, as well as Microsoft WINDOWS 56. The portable computer's remote display applications are run on WINDOWS. WINDOWS allows the GUI $42_2$, which is resident in the chassis computer 14, to be displayed remotely on the display 24 (not shown) of the portable computer 22. The operator uses the GUI $42_2$ to view and modify the operation of modules 16. When the portable computer 22 is in the WINDOWS environment, other WINDOWS applications may run concurrently, such as communications with the remote CIS 30. A package of products available from QNK, Inc. are used to generate and operate the remote GUI in the portable computer 22. The package of products includes PHOTON, PHINDOWS and PH RELAY. PHOTON generates the GUI, PHINDOWS runs the GUI in the portable computer 22, and PH RELAY provides the communications therebetween. PHOTON is resident in the operating system 44 of the chassis computer 14, PH RELAY is another software process $42_6$, and PHINDOWS is resident within the software 50 of the portable computer 22. The GUI software process $42_2$ may optionally be used to provide a local display 90 which would duplicate the functions of the remote GUI in the portable computer 22. In one preferred embodiment of the invention, each module 16 is associated with an object in C++.

FIG. 8A shows major hardware components of a module 16 that function in the dependent mode including a connector 58, chassis presence detection circuitry 60, an embedded, dedicated processor/controller 66 and a memory 68. The connector 58 is a "Make First Break Last" (MFBL) connection device which allows insertion and extraction of the module 16 without removing power from its critical circuit components. The chassis presence detection circuitry 60 is wired to the connector 58 and is used to determine whether the module 16 is inserted into the chassis 12. In the dependent mode, the processor/controller 66 receives power from the chassis 12 and sends its patient data to the storage device 18 of the chassis computer 14.

In the dependent mode, the module 16 uses the memory 68 as a temporary buffer memory to hold the data until it is sent out to the chassis 12. The chassis 12 continuously polls the module 16 for data in the memory 68. In the dependent mode, patient data is not accumulated in the memory 68. All patient data includes a time stamp.

FIG. 8B shows major hardware components of a module 16 which function in the independent mode, including a connector 58, chassis presence detection circuitry 60, a power source 62, a power converter and regulator 64, an embedded, dedicated processor/controller 66, a memory 68, a module front panel 33 (shown in detail in FIG. 5) and wireless LAN circuitry (not shown) connected to an antenna 70 for communicating with the assigned chassis 12. (The communications between a chassis 12 and its assigned modules 16 occur in a private network.) The power source 62 supplies power to the module 16 when it is not inserted into the chassis 12. In one preferred embodiment of the invention, the power source 62 is a lead-acid battery with an output voltage of 13.8 V DC (the float voltage for a typical lead-acid battery). The power source 62 is connected to the converter 64 which converts the power source raw voltage to a regulated voltage for use by the critical circuit components of the module 16. When using the above-described power source, the converter 64 is a DC/DC converter. The processor/controller 66 is a microprocessor-based device which is responsible for processing signals from external sensors and/or controlling external therapeutic devices. The processor/controller 66 contains a limited version of the module's complete control program which is stored in the respective chassis software process $42_{mx}$. Thus, when the module 16 is in the independent mode, it can execute some, but not all, of the control functions as when it is in the dependent mode. The processor/controller 66 is also responsible for communicating with one of two external channels. Channel 1 is a bus to the connector 58 for hardwired serial communication with the chassis 12. Channel 2 is a bus to the antenna 70 for wireless serial communication with the chassis 12 when the module 16 is not inserted into the chassis 12. The chassis presence detection circuitry 60 informs the processor/controller 66 as to which channel should be used. The module front panel 33 is connected to the processor/controller 66 and is described in detail above. The control keys 38 on the front panel 33 are used to operate the module 16 when it is not inserted into the chassis 12. Thus, the control keys 38 are active only in the independent mode. The control keys 38 are specific to the module function.

In the independent mode, the memory 68 is used for two functions. First, the memory 68 is used as a temporary buffer memory to store the patient data until it is sent out to the chassis 12 in response to a polling signal from the chassis 12 for storage in the chassis storage device 18. Thus, when a wireless LAN is installed in the module 16 and chassis 12 and properly functioning in both, the patient data is transferred in the same general manner as in the dependent mode. Second, if there is no active communication link between the chassis 12 and the module 16, the memory 68 stores the accumulated patient data for subsequent downloading to the chassis 12 upon reestablishment of the communication link, or upon reinsertion of the module 16 into the chassis 12. There may be no active communication link because the chassis 16 and/or module 16 do not include wireless communication means, or because the wireless communication means in the chassis and/or module are not functioning properly. Module polling does not occur if the chassis 12 and/or module 16 do not include wireless communication means. Also, polling does not occur if initial communications cannot be established between a chassis 12 and module 16. In either of these instances, the newly acquired patient data is accumulated in the memory 68 and is subsequently downloaded to the chassis 12 upon reinsertion of the module 16 into the chassis 12. If module polling has successfully begun but is subsequently interrupted due to a problem in a wireless communication process, the patient data is also accumulated in the memory 68 and is subsequently downloaded to the chassis 12 upon reestablishment of communications. For subsequent (newly acquired) data, the memory 68 is used as a temporary buffer memory to store the patient data until it is sent out to the chassis 12 in response to new polling signals from the chassis 12. Alternatively, the accumulated patient data may be downloaded after the module 16 is reinserted into the chassis 12, but newly acquired data would be immediately communicated upon receiving new polling signals.

The module 16 thus operates in a manner that ensures that no patient data is lost, either as a result of breaks in communication, or a result of plugging in or unplugging a module 16 from a chassis 12. Since all patient data includes a time stamp, any periods of data missing from the data files in the chassis storage device 18 can be filled in from data stored in the module 16 during the missing periods.

FIG. 9 further illustrates how the components of the subsystem 11 function together. The chassis computer 14 includes multiple serial ports that interface with the modules 16, a wireless LAN 46 and the portable computer 22. The chassis computer 14 also includes parallel ports to accommodate manual controls 72 and an optional printing device 74. The manual controls 72 include local pushbuttons for allowing an operator to have limited control of the modules 16 when a portable computer 22 is not present, and an audible alarm to signal a module alarm condition. When an alarm condition occurs, the chassis computer 14 automatically alerts a predesignated portable computer 22 to that fact. The printing device 74 may be a strip chart recorder which is local to the chassis 12 to provide a hard copy of patient data. The chassis computer 14 is also connected to a power supply 76 which supplies power to (a) whatever modules 16 are connected to the chassis 12, (b) the portable computer 22 when it is hard docked to the chassis 12, (c) other components connected to the chassis computer 14, and (d) an internal rechargeable battery 86 for use as a back-up power supply for the chassis 12 (the power supply 76 maintaining a full-charge on the battery). A keyboard 78 and bar code wand 80 are provided for use with the portable computer 22 when it is hard docked to the chassis 12. Furthermore, the chassis computer 14 is connected to a memory 84 for storing data received by the modules 16. When the portable computer 22 requests historical data from the modules 16, the data is retrieved from the memory 84.

To track changes to operating parameters of the modules 16, a data log or audit trail 88 is stored at the chassis 12. The audit trail 88 includes at least the following information:

1. User Name and password or ID of the clinician user who made a change.
2. Date and Time of change.
3. Name of the parameter or function that was accessed.

The audit trail 88 contains the previous parameter setting prior to the change, and a data field for the new parameter. Data encryption software is preferably used when changing operating parameters to ensure data integrity and eliminate data tampering.

In one preferred embodiment of the invention, the chassis computer 14 is an IBM-PC compatible containing 4 Megabytes of dynamic RAM, a 3.5" hard disk and sixteen serial channels, and the portable computer 22 is a Model IS-948i, manufactured by Admit, Inc., San Pedro, Calif. which includes PCMCIA Type II and III cards; a touch screen/flat panel display with a tethered pen; bar code input capabilities; a spread spectrum transceiver; and ability to communicate with wide area networks, including ARDIS radio, RAM Mobile Data Radio and CDPD Cellular Radio.

If the module is a patient monitoring sensor module, it may monitor any of the following body parameters: breathing rate, pulse rate, body temperature, blood pressure, urinary discharge, blood oxygen levels (oximeter), ECG waves, EKG waves, or EEG waves. It may also perform oxygen analysis, fetal monitoring, dental patient monitoring, or multi-gas analysis, as well as many other functions that would be apparent to one skilled in the art. If the module 16 is a therapy-providing module, it may perform one or more of the following functions: maintaining blood sugar, providing electric nerve stimulation, providing physical therapy, providing insulin, ventilating, nebulizing, providing chemotherapy, injecting via a syringe, humidifying, respirating, and operating a heating pad, as well as many other functions that would be apparent to one skilled in the art. If the module 16 is an accessory module, it may perform one or more of the following medical functions: collect urine, provide drinking water to the patient, remove fluid from the patient using a suction pump, perform vision, eye or hearing tests, or pump breast milk, as well as many other functions that would be apparent to one skilled in the art. The module may also be a peripheral accessory such as a printer, intercom, networking device, modem, magnetic card reader, voice recognition device, memory card reader, strip chart recorder, or telephone. Examples of such modules are further described in related U.S. patent application Ser. No. 08/224,444.

Operating parameters of the various types of modules referred to above are well known in the art. Accordingly, a detailed listing of settings, parameters, alarm values, alarm thresholds, and control functions is not provided.

Each module 16 includes a module software driver which contains all of the code required to operate the particular module. The code includes a control portion and a user interface portion. The control portion is responsible for the module programming instructions and acts on information supplied through the user interface portion to accomplish the actual module control. Once a module 16 is programmed, it can operate independently, and without the need for further commands from an external computer, such as the chassis computer 14. Such a module is further described in related U.S. patent application Ser. No. 08/224,444. However, the module described in the previous application cannot be operated independent of a chassis in the same manner as a module in the present invention because the module in the previous application does not have an independent power source or means to communicate with a remote source, or the type of memory, control keys, status displays and display which are necessary for independent operation.

Notwithstanding this difference, the module 16 in the present invention may be reprogrammed in the same manner as the module in related U.S. patent application Ser. No. 08/224,444. As described above, the portable computer 22 may send control signals to a module 16 to set or modify the module operating parameters. In some instances, setting or modifying operating parameters is a simple process that does not require reprogramming module controller circuitry (stored in the processor/controller 66). In other instances, setting or modifying operating parameters requires making changes in the underlying programming code or programming instructions of the modules 16. That is, it may be necessary to reprogram the operating instructions. The portable computer 22 may perform either function. One example of modifying an operating parameter is changing the configuration of an EKG module from a Lead I configuration to a Lead II configuration. Another example of modifying an operating parameter is changing the high and low alarm limit of a heart rate monitor.

In operation, the modules's processor/controller 66 provides operation and control functions when a module 16 is in either the independent or dependent mode. When the module operates in the dependent mode, the chassis 12 provides power, memory, communications and other needs of the module 16.

To seamlessly switch between the independent and dependent mode of module operation without any breaks in operation or collection of data, the circuit board for the chassis 12 includes a hardware interrupt line for signaling when a module 16 is inserted or removed. The interrupt line is normally high when a module 16 is plugged into the chassis 12. The interrupt line goes low when the module 16 is removed. Likewise, the module 16 has a port which is either high or low, depending upon whether the module 16 is plugged into, or unplugged from the chassis 12. When the status of the interrupt line and module port changes, the appropriate circuitry in both the chassis 12 and the module 16 switch over to their new mode, as fully described above. For example, when an active module 16 is removed from the chassis 12 (switching from dependent to independent mode), the module 16 automatically switches on its power source 62 and display panel 34. Wireless communications means in the module 16 and chassis 12 are initiated. In one embodiment of the invention, the module 16 establishes a private LAN link with its assigned chassis 12. If a portable computer 22 is currently monitoring a module 16 when the module 16 is switched from dependent to independent mode, module data is continuously sent to the chassis 12 for retrieval by the portable computer 22. When an independently operating module 16 is plugged into the chassis 12 (switching independent to dependent mode), the module 16 automatically switches over to receive power from the chassis power supply 76 and to display selected data on a chassis display. Any data accumulated in the memory 68 due to a break in communications or due to the absence of wireless communications means are downloaded to the chassis storage device 18. Subsequent data is automatically routed to the chassis storage device 18.

The communications protocol for allowing a portable computer 22 to retrieve patient data from modules 16 is preferably performed by a selective polling procedure, as follows:

1. A request is entered into the portable computer 22 to receive module data regarding PATIENT X.

2. The request is sent over the network described above and is received by each chassis 12 which are nodes on the network. The chassis 12 or plural chassis 12 which were previously assigned to PATIENT X respond to the request by returning data for each module 16 that is associated with the chassis 12 and assigned to PATIENT X.
   a. If the module 16 for PATIENT X is operating in the dependent mode, the data is retrieved from a data file set up for PATIENT X in the storage device 18, and is sent to the portable computer 22 for display thereon. (The data file is continuously updated by periodically polling the module memory 68 for patient data.)
   b. If the module 16 is operating in the independent mode, the chassis 12 also retrieves the data from the data file. (Again, the data file is being continuously updated by periodically polling the module memory 68 for patient data.) Thereafter, the chassis 12 sends the data in the patient file to the portable computer 22 for display thereon.

To minimize the risk that the wrong patient data is relayed to the portable computer 22, the remotely operating modules 16 send their assigned patient information along with the data, and the chassis computer 14 checks the patient information against the patient name originally requested by the portable computer 22. In steps 2a. and 2b., the data transfer between modules 16, the chassis 12 and the portable computer 22 occur at sufficiently high speed so as to appear to be in real time.

If a particular portable computer 22 is set up to monitor a particular patient, any alarms associated with that patient are immediately communicated to the chassis 12 and sent to the portable computer 22.

Instead of requesting communications with a particular module 16 or modules 16 assigned to a particular patient, the clinician user may request to view all modules 16 which have currently active alarms. The communications protocol is the same as described above, except that nodes are searched for all chassis 12 having actively alarmed modules 16, instead of a chassis 12 assigned to a particular patient. If authorized, the clinician user may silence selected alarms through the portable computer 22.

Other communications protocols which accomplish the same results as described above are within the scope of the invention. While the present communications protocol requires that the chassis 12 and chassis computer 14 be used as an interface between a portable computer 22 and the modules 16, the modules 16 themselves may alternatively become nodes of a central LAN. A central LAN link would be used to communicate the module data to its respective chassis 12, or to communicate the module data directly to the requesting portable computer 22 without routing the module data through its chassis 12.

As described above, all of the portable computers 22 are preferably identical to each other. A variety of different protocols are possible to initiate interaction between a portable computer 22 and the modules 16 dedicated to a particular patient. The following are examples of such protocols:

1. When the portable computer 22 is turned on or placed in a patient locating mode, the portable computer 22 queries all LAN nodes (e.g., all chassis 12) for patient name information and displays a listing of all patients on the network. The clinician user selects the patient or patients that are to be monitored and the appropriate module data appears on the display 24 of the portable computer 2. The clinician user types a patient name into the portable computer 22, a query is sent to all LAN nodes to locate those assigned to the patient, and the appropriate data appears on the display 3. The clinician user selects a floor of a hospital and a prestored floor plan appears on the display 24. The floor plan shows the location of all chassis along with the patient name assigned to each chassis 12 (as determined by the polling procedure described above). The clinician user selects the desired patient(s) and the display 24 switches over to show the module data for the selected patient(s).

Security for the system of the present invention is provided using name and password procedures. For example, before a portable computer 22 can retrieve data from a module 16 or change an operating parameter of a module 16, the clinician user must enter their user name and/or password. The user name and/or password is verified by the CIS 30, or by other suitable means. An additional level of security is provided by using portable computers 22 because the module operating parameters can only be changed through the portable computer 22 (in the embodiment wherein the chassis 12 does not include the optional local display 90), and because distribution of the portable computers 22 will be limited and controlled.

FIG. 10 shows a patient monitoring system 11' wherein plural patients (e.g., two patients 92 and 94) share a single chassis 12. The left side of the chassis 12 is assigned to patient 92 and the right side of the chassis 12 is assigned to patient 94. In FIG. 10, patient 92 is at his bedside and the modules $16_1$ and $16_2$ assigned to patient 92 are plugged into the chassis 12 and are operating in the dependent mode. Patient 94 is being transported from his bedside. Accordingly, the modules $16_3$ and $16_4$ assigned to patient 94 are operating in the independent mode. The portable computer 22 is currently remotely monitoring only patient 94. A split screen display with a major and minor window may be used to monitor both patients. Only modules 16 shown in the major window can be modified.

While the present invention preferably performs certain communications functions in a wireless manner, it is within the scope of the invention to perform the functions in a hardwired manner.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A patient monitoring system comprising:
   (a) one or more patient care modules, each module being fully operational in either an independent or dependent mode;
   (b) a point of care chassis having a chassis computer and a power supply, said chassis adapted to physically receive and communicate with one or more of the modules when operating the one or more modules in the dependent mode, the one or more modules being connected to the chassis computer and the power supply in the dependent mode, said chassis also adapted to remotely communicate with the one or more modules when operated in the independent mode; and
   (c) a portable computer for communicating with the one or more modules when the one or more modules are in either the independent or dependent mode.

2. A patient monitoring system according to claim 1 further comprising a plurality of point of care chassis, each chassis being associated with a patient, said one or more modules, being associated with and in communication with a predesignated one said chassis, said one or more modules further being assigned to a predetermined patient, and a plurality of portable computers, each portable computer being adapted to communicate with any of the modules.

3. A patient monitoring system according to claim 2 further comprising:
   (d) a clinical information system in communication with each of the chassis, the clinical information system including patient file records for each predetermined patient, each portable computer including means for communicating with the clinical information system to obtain access to the patient file records.

4. A patient monitoring system according to claim 3 wherein the clinical information system includes a file server, and each portable computer communicates with the file server through a wired or wireless local area network.

5. A patient monitoring system according to claim 4 wherein each portable computer includes means to emulate a workstation or terminal to interface with the file server of the clinical information system.

6. A patient monitoring system according to claim 3 wherein the clinical information system receives and stores information sent from each module in the patient file record for each predetermined patient.

7. A patient monitoring system according to claim 3 wherein each portable computer communicates with the clinical information system either directly or through one of said chassis.

8. A patient monitoring system according to claim 2 wherein the system is adapted so that each portable computer may simultaneously communicate with the one or more modules.

9. A patient monitoring system according to claim 8 wherein each of the one or more modules includes means for modifying module control parameters, each portable is computer adapted to modify the control parameters when the one or more modules are in either the independent or dependant mode.

10. A patient monitoring system according to claim 9 wherein each portable computer includes a graphical user interface display mode for use in modifying the control parameters.

11. A patient monitoring system according to claim 2 wherein one or more of the modules are adapted to collect patient data, each of the one or more modules including an alarm which is enabled when the patient data is outside of a predetermined range, the chassis computer including means for automatically communicating the alarm to a predesignated one of said portable computers when the alarm is enabled.

12. A patient monitoring system according to claim 1 wherein the portable computer communicates with the one or more modules through the chassis and chassis computer when the modules are in either the independent or dependent mode.

13. A patient monitoring system according to claim 12 wherein the portable computer and the chassis each include wireless communication means for communicating with the one or more modules when the one or more modules are in the independent mode.

14. A patient monitoring system according to claim 1 wherein one or more of the modules are adapted to collect patient data, the portable computer including means for monitoring the patient data when the module is in either the independent or dependent mode.

15. A patient monitoring system according to claim 14 wherein the chassis further includes a storage device, and the one or more modules, when operated in the dependent mode, receive power from the power supply of the chassis, receive control signals from the chassis computer, and send collected data to the storage device for retrieval by the portable computer.

16. A patient monitoring system according to claim 1 further comprising:
   (d) a docking station connected to the chassis for physically receiving the portable computer and allowing hardwired communication between the portable computer and the one or more modules through the chassis and the chassis computer.

17. A patient monitoring system according to claim 1 wherein the portable computer further includes means for controlling the one or more modules when the one or more modules are in either the independent or dependent mode.

18. A patient monitoring system according to claim 1 wherein the one or more modules are selected from the group consisting of a patient monitoring sensor module, a therapy-providing module, and an accessory module.

19. A patient monitoring system according to claim 1 wherein each of the one or more modules includes an internal power source, a dedicated processor/controller for controlling the operation of the module, a dedicated storage device for storing patient data collected by the module, an internal display, and means for remotely communicating with the chassis, wherein the internal power source, the dedicated processor/controller, the dedicated storage device, the internal display and the remote communications means are adapted to be used when operating the module in the independent mode.

20. A patient monitoring system according to claim 1 wherein one or more of the modules are adapted to collect patient data, each module including a power source and the chassis and each module including a patient data storage device, the capacity of the chassis power supply and storage device being greater than the capacity of the module power source and storage device.

21. A patient monitoring system according to claim 1 wherein one or more of the modules are adapted to collect patient data, the portable computer being adapted to communicate with the one or more modules to retrieve historical patient data collected from the one or more modules.

22. A patient monitoring system according to claim 1 further comprising:

(d) one or more third party medical devices for collecting patient data and communicating the collected data to the chassis, wherein the portable computer is adapted to communicate with the chassis to retrieve the patient data collected from the one or more modules and from the one or more third party medical devices.

23. A patient monitoring system according to claim 1 further comprising a plurality of point of care chassis, each chassis being associated with a plurality of patients, said one or more modules, being associated with and in communication with a predesignated one of said chassis, said one or more modules further being assigned to a predetermined patient, and a plurality of portable computers, each portable computer being adapted to communicate with any of the modules, including a plurality of modules associated with different patients.

24. A patient monitoring system according to claim 1 wherein one or more of the modules are adapted to collect patient data, each module including a power source, a memory for storing patient data, and a chassis presence detector for detecting whether the module is physically connected to the chassis, each module being adapted to store the patient data in the memory upon detection by the chassis presence detection circuitry that the module is not physically connected to the chassis.

25. A patient monitoring system according to claim 1 wherein one or more of the modules are adapted to collect patient data, each module including a power source, a memory for storing patient data, and a chassis presence detector for detecting whether the module is physically connected to the chassis, each module being adapted to store the patient data in the memory upon detection by the chassis presence detection circuitry that the module is not physically connected to the chassis or upon detection of a break in remote communications between the module and the chassis.

26. A patient monitoring system according to claim 25 wherein the one or more modules which collect patient data are adapted to download the stored patient data upon being physically connected to the chassis or upon reestablishment of remote communications between the module and the chassis.

* * * * *